US010849557B2

(12) United States Patent
Keating et al.

(10) Patent No.: US 10,849,557 B2
(45) Date of Patent: Dec. 1, 2020

(54) FABRIC-BASED ITEMS WITH STRETCHABLE BANDS

(71) Applicant: Apple Inc., Cupertino, CA (US)

(72) Inventors: Steven J. Keating, Sunnyvale, CA (US); Daniel D. Sunshine, Sunnyvale, CA (US); Benjamin J. Grena, San Francisco, CA (US); Daniel A. Podhajny, San Jose, CA (US); Jerzy S. Guterman, Sunnyvale, CA (US); Jessica J. Lu, Mountain View, CA (US); David M. Kindlon, Felton, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/140,419

(22) Filed: Sep. 24, 2018

(65) Prior Publication Data

US 2019/0298265 A1 Oct. 3, 2019

Related U.S. Application Data

(60) Provisional application No. 62/649,505, filed on Mar. 28, 2018.

(51) Int. Cl.
*A61B 5/00* (2006.01)
*A61B 5/0205* (2006.01)
(Continued)

(52) U.S. Cl.
CPC ............. *A61B 5/6831* (2013.01); *A61B 5/01* (2013.01); *A61B 5/0205* (2013.01);
(Continued)

(58) Field of Classification Search
CPC .................................................. A61B 5/6831
(Continued)

(56) References Cited

U.S. PATENT DOCUMENTS

| 6,595,929 B2 | 7/2003 | Stivoric et al. |
| 6,685,634 B1 | 2/2004 | Fry |

(Continued)

FOREIGN PATENT DOCUMENTS

| CN | 101528282 A | 9/2009 |
| CN | 106137179 A | 11/2016 |

(Continued)

*Primary Examiner* — Qutbuddin Ghulamali
(74) *Attorney, Agent, or Firm* — Treyz Law Group, P.C.; G. Victor Treyz; David K. Cole

(57) ABSTRACT

A fabric-based item may be provide with a stretchable band. The stretchable band may be formed from a ring-shaped strip of stretchable fabric having an opening configured to fit around a body part of a user. Circuitry may be coupled to strands of material in the stretchable band. The circuitry may include sensor circuitry for making measurements on the body part such as electrocardiogram measurements, blood pressure measurements, and respiration rate measurements. Wireless communications circuitry in the fabric-based item may be used to communicate wirelessly with external electronic equipment. A wireless power transmitting device may transmit wireless power. A coil formed from conductive strands in the fabric-based item may be used by wireless power receiving circuitry in the fabric-based item to receive the wireless power. The coil may have one or more turns that run around the ring-shaped strip of stretchable fabric.

20 Claims, 6 Drawing Sheets

(51) Int. Cl.
- A61B 5/021 (2006.01)
- A61B 5/024 (2006.01)
- A61B 5/0408 (2006.01)
- A61B 5/08 (2006.01)
- D03D 1/00 (2006.01)
- D03D 7/00 (2006.01)
- D03D 15/08 (2006.01)
- H04B 1/3827 (2015.01)
- H04W 4/80 (2018.01)
- A61B 5/01 (2006.01)
- A61B 5/113 (2006.01)
- D02G 3/44 (2006.01)

(52) U.S. Cl.
CPC ...... *A61B 5/02141* (2013.01); *A61B 5/02438* (2013.01); *A61B 5/02444* (2013.01); *A61B 5/0408* (2013.01); *A61B 5/0816* (2013.01); *A61B 5/113* (2013.01); *A61B 5/6804* (2013.01); *A61B 5/6805* (2013.01); *A61B 5/6823* (2013.01); *D02G 3/441* (2013.01); *D03D 1/0088* (2013.01); *D03D 7/00* (2013.01); *D03D 15/08* (2013.01); *H04B 1/385* (2013.01); *H04W 4/80* (2018.02); *A61B 5/021* (2013.01); *A61B 5/681* (2013.01); *A61B 5/6824* (2013.01); *A61B 2503/10* (2013.01); *A61B 2503/12* (2013.01); *A61B 2505/07* (2013.01); *A61B 2505/09* (2013.01); *A61B 2560/0214* (2013.01); *A61B 2560/0468* (2013.01); *A61B 2562/0214* (2013.01); *A61B 2562/0219* (2013.01); *A61B 2562/125* (2013.01); *A61B 2562/164* (2013.01); *D03D 2700/0103* (2013.01); *D03D 2700/0166* (2013.01); *D10B 2331/02* (2013.01); *D10B 2331/10* (2013.01); *D10B 2401/18* (2013.01); *D10B 2509/00* (2013.01)

(58) Field of Classification Search
USPC .................................................. 340/539.12
See application file for complete search history.

(56) References Cited

U.S. PATENT DOCUMENTS

| | | | |
|---|---|---|---|
| 2004/0237494 A1* | 12/2004 | Karayianni | D02G 3/441 57/212 |
| 2007/0293781 A1 | 12/2007 | Sims et al. | |
| 2008/0079565 A1* | 4/2008 | Koyama | G16H 40/63 340/539.12 |
| 2008/0282665 A1* | 11/2008 | Speleers | D02G 3/12 57/212 |
| 2008/0294019 A1 | 11/2008 | Tran | |
| 2013/0146659 A1 | 6/2013 | Zhou et al. | |
| 2014/0143064 A1 | 5/2014 | Tran | |
| 2014/0180019 A1 | 6/2014 | Martinez et al. | |
| 2014/0241555 A1 | 8/2014 | Terlizzi | |
| 2015/0364938 A1 | 12/2015 | Lapetina et al. | |
| 2016/0000374 A1* | 1/2016 | Dandekar | A61B 5/0476 600/301 |
| 2016/0058133 A1 | 3/2016 | Fournier | |
| 2016/0058375 A1 | 3/2016 | Rothkopf | |
| 2016/0091864 A1 | 3/2016 | Yang et al. | |
| 2016/0327979 A1 | 11/2016 | Lettow | |
| 2017/0018843 A1* | 1/2017 | Kourti | H01Q 9/26 |

FOREIGN PATENT DOCUMENTS

| | | |
|---|---|---|
| CN | 206183262 U | 5/2017 |
| CN | 206586944 U | 10/2017 |
| CN | 206629999 U | 11/2017 |

* cited by examiner

FABRIC-BASED ITEMS WITH STRETCHABLE BANDS

This application claims priority to U.S. provisional patent application No. 62/649,505 filed Mar. 28, 2018, which is hereby incorporated by reference herein in its entirety.

FIELD

This relates generally to items with fabric and, more particularly, to items with stretchable fabric.

BACKGROUND

It may be desirable to form items using materials such as fabric. For example, wearable items may be formed from fabric. Some wearable items may include sensing circuitry. Control circuitry in the item may use the sensing circuitry to gather information on a user's health and other data. Output devices in a wearable item may provide output to a user.

If care is not taken, fabric-based items such as these may not offer desired features. For example, a fabric-based item with sensing circuitry may not be able to gather measurements accurately, may not be able to interact with external equipment effectively, or may be difficult for a user to keep clean.

SUMMARY

A fabric-based item may be provide with a stretchable band. The stretchable band may be formed from a ring-shaped strip of stretchable fabric having an opening configured to fit around a body part of a user. Circuitry may be coupled to strands of material in the stretchable band. The circuitry may include sensor circuitry for making measurement on the body part such as electrocardiogram measurements, blood pressure measurements, respiration rate measurements, and other measurements. When being worn on the body part of the user, the stretchable band may hold the sensor circuitry against the body part to facilitate gathering accurate measurements.

The fabric-based item may be configured to sustain relatively high temperatures such as those associated with laundering of clothing. For example, the fabric-based item may have supercapacitors for energy storage and other electrical components that can be laundered in hot water and dried in a clothes dryer without damage. To withstand damage when the fabric-based item is stretched, fabric may include strengthening strands and conductive strands may be provided with meandering paths and more slack than the strengthening strands.

Wireless communications circuitry in the fabric-based item may be used to communicate wirelessly with external electronic equipment. A coil formed from conductive strands in the fabric-based item may be used by wireless power receiving circuitry in the fabric-based item to receive wireless power. The coil may have one or more turns that run around the ring-shaped strip of stretchable fabric forming the stretchable band so that the coil surrounds a central opening in the stretchable band.

DETAILED DESCRIPTION

Figure 1:
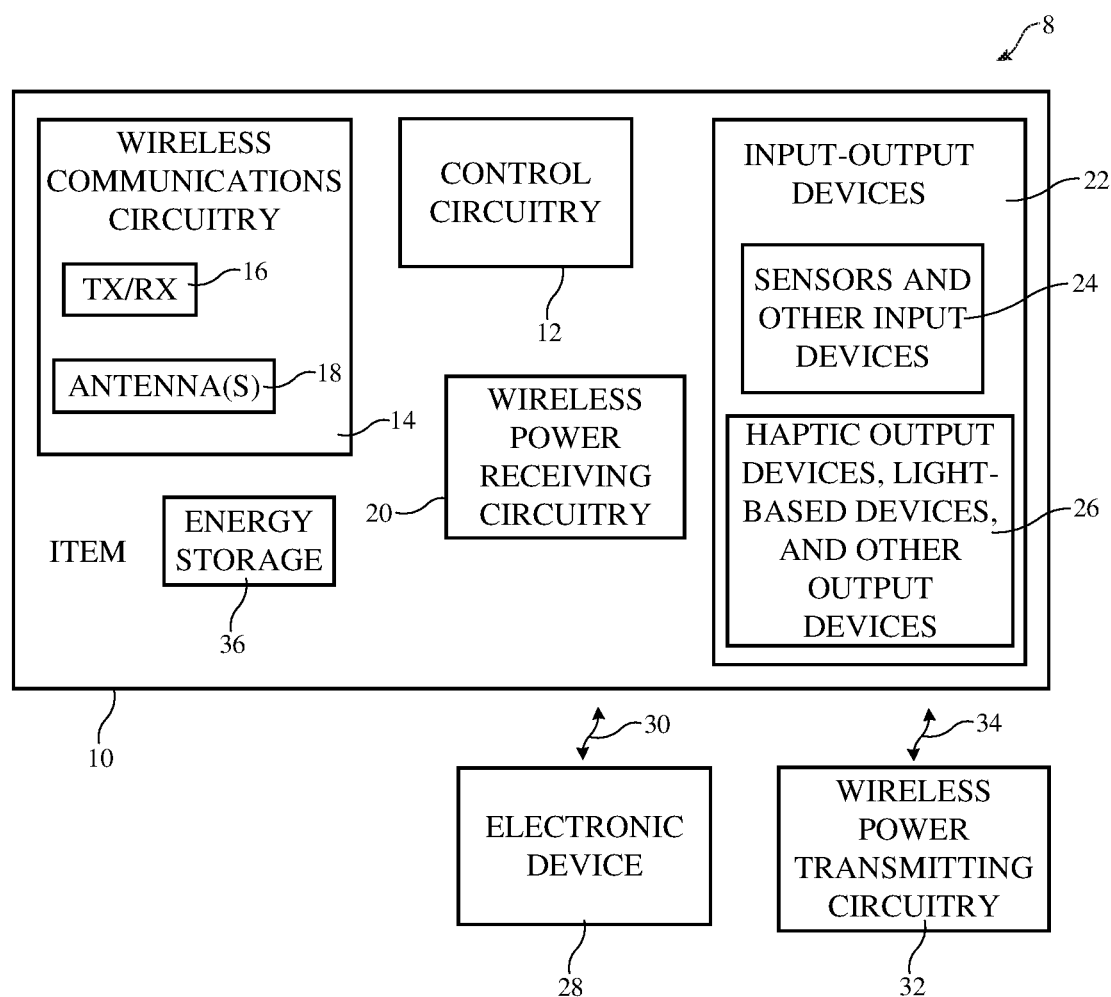
FIG. 1 is a schematic diagram of an illustrative fabric-based item in accordance with an embodiment.

A schematic diagram of an illustrative system that may contain items with fabric is shown in FIG. 1. As shown in FIG. 1, system 8 may include one or more fabric-based items such as fabric-based item 10 and additional equipment such as electronic device(s) 28 and wireless power transmitting circuitry 32. Item 10 may be a wearable device with elastic fabric. As examples, item 10 may be a wrist band with elastic fabric, a head band with elastic fabric, or other wearable item that includes elastic fabric (e.g., a hat, an undergarment worn on a user's torso or lower body, a shirt, pants, shorts (e.g., bicycle shorts, board shorts, or other snugly fitting clothing), yoga clothing or other athletic attire, an arm band, an elastic belt, a sock, a glove, etc. If desired, item 10 may incorporate some or all of the functionality of other electronic devices. For example, item 10 may be an electronic device or an accessory for an electronic device such as a laptop computer, a computer monitor containing an embedded computer, a tablet computer, a cellular telephone, a media player, or other handheld or portable electronic device, a smaller device such as a wrist-watch device, a pendant device, a headphone or earpiece device, a device embedded in eyeglasses or other equipment worn on a user's head, or other wearable or miniature device, a television, a computer display that does not contain an embedded computer, a gaming device, a remote control, a navigation device, an embedded system such as a system in which item 10 is mounted in a kiosk, in an automobile, airplane, or other vehicle, equipment incorporated into furniture, a strap for a bag or other enclosure, other electronic equipment, or may be equipment that implements the functionality of two or more of these devices. Configurations in which item 10 is a wearable item with an elastic fabric band may sometimes be described herein as an example.

Item 10 may communicate wirelessly with external accessories and other devices such as device 28 (e.g., an item such as item 10 or other electronic equipment). In some arrangements, energy storage devices in item 10 may be provided with wireless power. For example, wireless power transmitting circuitry 32 may supply wireless power signals 34 (e.g., electromagnetic signals 34) that are received by wireless power receiving circuitry 20 in item 10.

Item 10 may include intertwined strands of material that form fabric such as stretchable fabric (e.g., elastic fabric formed using stretchable strands of material). Items such as item 10 may therefore sometimes be referred to as fabric-based items, stretchable-fabric items, stretchable-fabric-based electronic devices, etc. In some configurations, stretchable fabric for item 10 may form a stretchable band (e.g., a waistband, wristband, headband, armband, or other stretchable band in an item of clothing). Item 10 may be soft (e.g., item 10 may have a fabric surface that yields to a light touch), may have a rigid feel (e.g., the surface of item 10 may be formed from a stiff fabric), may be coarse, may be smooth, may have ribs or other patterned textures, and/or may be formed as part of a device that has portions formed from non-fabric structures of plastic, metal, glass, crystalline materials, ceramics, or other materials.

The strands of material in the stretchable fabric of item 10 may be single-filament strands (sometimes referred to as fibers or monofilaments), may be yarns or other strands that have been formed by intertwining multiple filaments (multiple monofilaments) of material together, or may be other types of strands (e.g., tubing). Monofilaments for the fabric of item 10 may include polymer monofilaments and/or other insulating monofilaments and/or may include bare wires and/or insulated wires. Monofilaments formed from polymer cores with metal coatings and monofilaments formed from three or more layers (cores, intermediate layers, and one or more outer layers each of which may be insulating and/or conductive) may also be used.

Yarns for the fabric of item 10 may be formed from polymer, metal, glass, graphite, ceramic, natural materials as cotton or bamboo, or other organic and/or inorganic materials and combinations of these materials. Conductive coatings such as metal coatings may be formed on non-conductive material. For example, plastic yarns and monofilaments may be coated with metal to make them conductive. Reflective coatings such as metal coatings may be applied to make yarns and monofilaments reflective. Yarns may be formed from a bundle of bare metal wires or metal wire intertwined with insulating monofilaments (as examples).

Strands of material may be intertwined to form fabric for item 10 using intertwining equipment such as weaving equipment, knitting equipment, or braiding equipment. Intertwined strands may, for example, form woven fabric, knit fabric, braided fabric, etc. Conductive strands and insulating strands may be woven, knit, braided, or otherwise intertwined to form contact pads that can be electrically coupled to conductive structures in item 10 such as the contact pads of an electrical component. The contacts of an electrical component may also be directly coupled to an exposed metal segment along the length of a conductive yarn or monofilament.

Conductive and insulating strands may also be woven, knit, or otherwise intertwined to form conductive paths. The conductive paths may be used in forming signal paths (e.g., signal buses, power lines, etc.), may be used in forming part of a capacitive touch sensor electrode, a resistive touch sensor electrode, a force sensor electrode, or other input-output device, or may be used in forming other patterned conductive structures. Conductive structures in the fabric of item 10 may be used in carrying power signals, digital signals, analog signals, sensor signals, control signals, data, input signals, output signals, radio-frequency signals such as antenna signals, or other suitable electrical signals.

Item 10 may include mechanical structures in addition to fabric such as polymer binder to hold strands in a fabric structure together, support structures such as frame members, housing structures (e.g., an electronic device housing), and other mechanical structures.

Item 10 may include circuitry such as wireless communications circuitry 14, control circuitry 12, input-output devices 22, energy storage circuitry 36, and wireless power receiving circuitry 20. This circuitry may include electrical components that are coupled to fabric in item 10, electrical components embedded in strands of material in fabric in item 10, electrical components that are housed within an enclosure formed by fabric and/or electrical components housed within an enclosure formed using other housing structures such as housing walls formed from plastic, metal, glass, ceramic, or other materials, electrical components that are attached to fabric in item 10 using welds, solder joints, adhesive bonds (e.g., conductive adhesive bonds such as anisotropic conductive adhesive bonds or other conductive adhesive bonds), crimped connections, or other electrical and/or mechanical bonds. The circuitry in item 10 may include metal structures for carrying current, electrical components such as integrated circuits, discrete components (e.g., capacitors, resistors, and inductors), light-emitting components, haptic output components, sensors, and/or other circuitry.

Input-output circuitry 22 may include sensors and other input devices 24, may include haptic output devices, light-based output devices (e.g., light-emitting diodes and/or lasers for displays or status indicators), and other output devices 26. Devices 22 may include, for example, light-emitting diodes, lasers, displays (e.g., displays formed from light-emitting diodes and/or lasers and/or displays formed from arrays of other pixels), speakers, microphones, buttons, tone generators, haptic output devices such as vibrators, force sensors, gas sensors, gas pressure sensors, temperature sensors, strain gauges, accelerometers, proximity sensors, touch sensors, ambient light sensors, digital image sensors, electrocardiogram (EKG) sensors, blood pressure sensors, blood flow sensors, blood oxygen sensors, heart rate sensors, respiration rate sensors based on accelerometers or other components, fingerprint sensors, gaze detection and eye and face sensing devices, magnetic sensors, other sensors, or sensors that include the capabilities of two or more of these sensors. Sensors in devices 22 may include sensing electrodes, which may be formed from conductive strands of material in fabric (e.g., sensor electrode pads formed from fabric), may be formed from metal traces on printed circuits, and/or may be formed from other sense electrode structures.

Control circuitry 12 may be formed from one or more integrated circuits such as microprocessors, microcontrollers, application-specific integrated circuits, digital signal processors, and/or other circuits. Control circuitry 12 may be used to gather information from user input circuitry, sensing circuitry such as touch sensors, force sensors, proximity sensors, and other sensing circuitry, and other input-output devices 22. Control circuitry 12 may be used to control the operation of item 10 based on this gathered information and/or based on other information by controlling electrically controllable (electrically adjustable) components in circuitry 12. The control circuitry may use communications circuitry such as wireless communications circuitry 14 to communicate with external equipment such as electronic device 28. Using wireless communications or wired communications, control circuitry 12 in item 10 may, if desired, provide information such as sensor information and/or other information gathered using input-output devices 22 to external equipment such as device 28 over communications such as path 30 (e.g., a wired or wireless path). For example, item 10 may send health data and other data to a device such as a cellular telephone or computer.

Wireless communications circuitry 14 may include transceiver circuitry such as transceiver circuitry 16. Transceiver circuitry 16 may include transmitter and/or receiver circuitry for sending and/or receiving wireless communication using one more antennas 18. Transceiver circuitry 16 may operate in any suitable communication band (e.g., cellular telephone communications bands, wireless local area network bands such as bands at 2.4 GHz and 5 GHz, communications at frequencies of between 700 MHz and 1 GHz, at least 500 MHz, at least 800 MHz, at least 1.5 GHz, at least 2 GHz, at least 10 GHz, at least 25 GHz, less than 100 GHz, less than 70 GHz, less than 10 GHz, less than 6 GHz, less than 3 GHz, less than 1 GHz, or other suitable wireless communications frequencies). Antennas 18 may include monopole antennas, dipole antennas, patch antennas, inverted-F antennas, loop antennas, slot antennas, other antennas, and/or antennas that include antenna resonating elements of more than one type (e.g., hybrid slot-inverted-F antennas, etc.). Antennas 18 may be formed from metal traces on printed circuits or other substrates, may include stamped metal parts, may include metal structures that form part of an enclosure or other supporting structure for item 10, may include wires and other conductive strands of material in fabric, and/or other conductive structures.

Wireless power receiving circuitry 20 may be configured to receive wireless power signals 34 from wireless power transmitting circuitry 32. In some configurations, wireless power transmitting circuitry 32 may be incorporated into a device such as device 28 that also includes radio-frequency wireless communications circuitry or other communications circuitry for communicating with item 10 over communications link 30. Wireless power transmitting circuitry 32 may transmit power wirelessly using inductive wireless power transfer, using capacitive wireless power transfer, and/or other wireless power transfer configurations (e.g., optical). With one illustrative configuration, wireless power receiving circuitry 20 includes a wireless power receiving circuit having a coil and associated circuitry (e.g., one or more capacitors) and includes a rectifier that converts received alternating-current power signals from the wireless power receiving circuit to direct-current power for powering item 10. In this type of configuration, wireless power transmitting circuitry 32 may include inverter circuitry that is used to supply alternating-current (AC) signals (e.g., alternating-current signals controlled via pulse-width modulation) to a wireless power transmitting circuit that includes one or more coils and one or more associated capacitors. During operation, the signals supplied by the inverter circuitry cause the coil(s) in the wireless power transmitting circuit to emit wireless power signals 34, which are received and converted to direct-current (DC) power by circuitry 20.

Direct-current power from circuitry 20 can be consumed by the components (load) of item 10 and may, if desired, be stored in one or more energy storage devices 36 for later use. Energy storage devices 36 may include batteries and capacitors. Capacitors for energy storage may be based on supercapacitor structures. Devices 36 may, for example, include super capacitor(s) such as electrostatic double-layer capacitors. Electrostatic double-layer capacitors (sometimes referred to as electrostatic double-layer super capacitors) are electrochemical capacitors in which energy is stored in a capacitor formed from relatively large electrodes that are bathed in electrolyte and separated by a small distance, allowing the capacitor to achieve high energy storage capacities. In some arrangements, super capacitors can withstand high temperatures without being damaged (e.g., at least 70° C. or at least 80° C.), allowing item 10 be washed and dried in a user's home washer and dryer.

Figure 2:
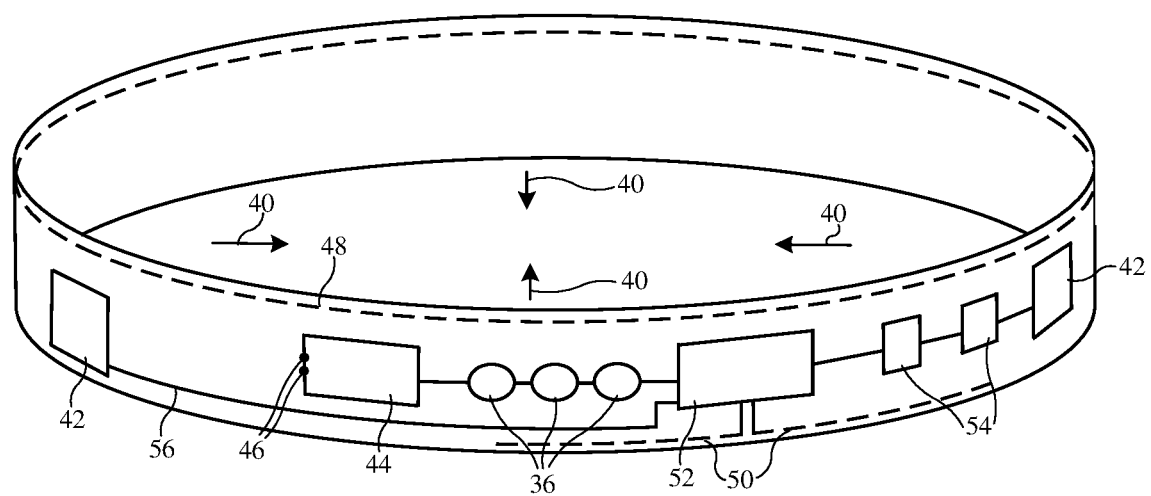
FIG. 2 is a perspective view of an illustrative item such as a band that is formed from elastic fabric in accordance with an embodiment.

Item 10 may include stretchable fabric. For example, item 10 may be a stretchable band of fabric or may include a stretchable band of fabric. A perspective view of item 10 in an illustrative configuration in which item 10 is formed from a stretchable fabric band is shown in FIG. 2. The band of item 10 of FIG. 2 is formed from a ring-shaped strip of stretchable fabric having an opening that is configured to receive a body part of a user. The band shape of item 10 of FIG. 2 allows item 10 to be worn on a body part of a user (e.g., a user's head, arm, wrist, waist, leg, ankle, finger, neck, torso, etc.). Item 10 may be stretched when being placed on a user's body. Due to the stretchable fabric of item 10, item 10 attempts to return to its original shape when released on the user's body part, pressing inwardly on the user's body in directions 40. When item 10 is held against the body of a user in this way, sensors (e.g., sensor electrodes) will be in close proximity to a user's skin and can gather measurements that might otherwise be difficult or impossible to gather (e.g., skin moisture measurements, EKG measurements, blood pressure measurements, etc.).

In the example of FIG. 2, item 10 includes electrical components coupled by paths such as paths 56. Paths 56 may include one or more conductive lines for carrying power signals, data signals, control signals, and/or other signals. The conductive lines may be formed from conductive strands of material in fabric, metal traces on printed circuits or other substrates, or other conductive path structures. Conductive strands or metal traces on a substrate may be configured to form sensor electrodes. For example, conductive strands may be used to form patch-shaped electrodes such as electrodes 42. If desired, patch-shaped electrodes such as electrodes 42 may be formed from metal traces on a flexible substrate, conductive polymer (e.g., an elastomeric polymer with conductive filler such as carbon-loaded elastomeric polymer, metal traces deposited by physical vapor deposition and/or electrochemical deposition, metal foil patches, conductive polymer that is deposited on fabric, and/or other conductive patch structures. Electrodes 42 may be coupled to components such as components 54 using conductive paths 56. For example, conductive polymer patches forming electrodes 42 may be shorted to wires or other conductive strands forming paths 56 so that components 54 can make sensor measurements using electrodes 42. Components 54 may include, for example, electrocardiogram (EKG) measurement circuitry for making EKG measurements using electrodes 42 and/or other circuitry (see, e.g., input-output devices 22 of FIG. 2).

One or more antennas 18 may be formed from conductive paths 50 (e.g., conductive strands in fabric, metal traces, etc.). Antenna(s) 18 may be coupled to wireless communications circuitry such as transceiver(s) 16 (e.g., transceiver circuitry in circuit 52). Circuit 52 and/or other circuitry in item 10 may include control circuitry 12 for controlling the operation of item 10 (e.g., for using an EKG sensor and/or other input-output devices 22 to gather input and provide a user with output).

Power may be received by item 10 using power circuit 44. Power circuit 44 may, if desired, receive wired power via terminals 46. Power circuitry 44 may also include wireless power receiving circuitry 20 and one or more wireless power receiving coils such as illustrative coil 48. Coil 48 may be formed from one or more conductive lines that run around item 10 (e.g., the ring-shaped stretchable fabric band of item 10 may include conductive strands of material such as insulated and/or bare wire that form a wireless power receiving coil with one turn, at least two turns, at least three turns, at least 10 turns, fewer than 15 turns, fewer than 8 turns, or other suitable number of turns).

Energy storage devices 36 may be charged by power received using power circuit 44 (e.g., received wireless power or wired power). Using an inductive charging coil such as coil 48 of FIG. 2, item 10 may receive wireless power from wireless power transmitting circuitry 32. If desired, circuitry 32 may be placed in proximity of a user's closet, furniture, or other clothing storage location so that item 10 (e.g., a wearable item such as an item of clothing) can be wirelessly powered during normal use (e.g., when stored overnight in a closet or piece of furniture).

Items such as item 10 of FIG. 2 may use devices 22 to gather any suitable input and provide any suitable output. As an example, item 10 may use blood pressure sensors to gather blood pressure information, may use heart rate sensors to gather heart rate information, may include blood sugar sensors for gathering blood sugar levels, may use blood oxygen sensors to measure a user's blood oxygen level, may use accelerometers to measure a user's activity, etc. If desired, accelerometers and/or other sensors may gather information on a user's respiration rate (e.g., by extracting respiration rate information from accelerometer readings). Health data, intentional user input (e.g., button press input on force sensors, touch sensors, and/or other input devices, voice commands gathered with a microphone, gesture input, tap input, etc.), environmental readings, and/or other information on the user and the user's surroundings may be gathered by devices 22 and processed by control circuitry 12. Control circuitry 12 may also use the output devices of input-output devices 22 to provide haptic output, audio output, visual output (e.g., status light indicator output, display output such as displayed images of text, graphics, and/or video, etc.), and/or other output may be provided.

In some configurations, item 10 may be used in isolation (e.g., as a wrist band with input and output capabilities). In other configurations, item 10 may operate in conjunction with external equipment (e.g., device 28 of FIG. 1). As an example, item 10 may gather health data and/or other information using input-output devices 22 and may provide this information to device 28 wirelessly. Device 28 can process this data and can take suitable action (e.g., by using its input-output devices to provide output to a user or by directing item 10 to provide output to the user using the input-output circuitry 22 of item 10).

Figure 3:
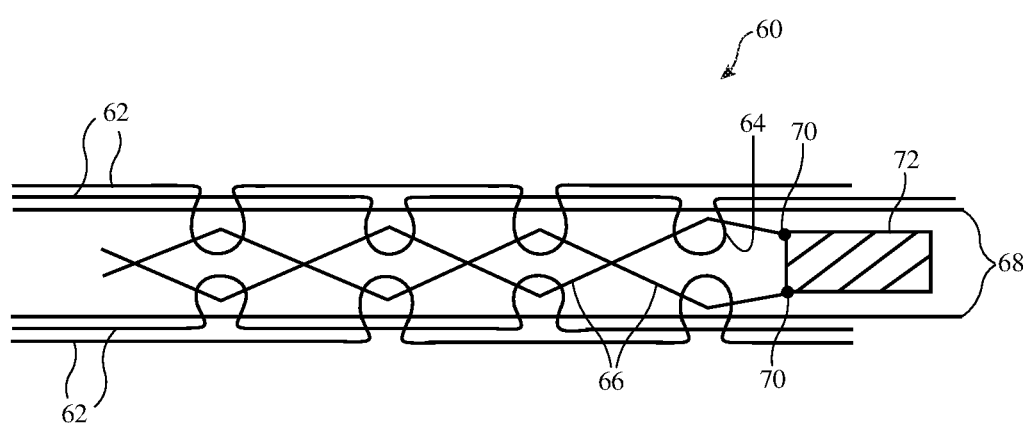
FIG. 3 is a side view of illustrative fabric with circuitry in accordance with an embodiment.

Item 10 may include fabric with one or more fabric layers. Item 10 may, as an example, include stretchable fabric such as the illustrative stretchable fabric shown in the cross-sectional side view of FIG. 3. As shown in FIG. 3, fabric 60 may include stretchable (elastic) strands of material such as stretchable strands 68. Strands 68 may, for example, be formed from an elastomeric polymer that can stretch and return elastically to its unstretched state (e.g., when strands 68 are not stretched more than their elongation-to-break limits). As an example, strands 68 may be formed from synthetic rubber or spandex (a copolymer of polyoxyethylene and polyurethane, sometimes referred to as Lycra® or elastane). Stretchable strands 68 may, as an example, be characterized by a high elongation-to-break value (e.g., at least 200%, at least 300%, at least 400%, less than 800%, less than 1000%, etc.). Fabric 60 may also have strands that are less stretchable, but that add strength to fabric 60 such as strengthening strands 62. Strands 62 may be stronger and less stretchable than strands 68. For example, strands 62 may be nylon strands or strands of other strong material and may be characterized by elongation-to-break values of 10-30%, at least 12%, at least 16%, less than 25%, less than 35%, less than 50%, less than 22%, etc. In some arrangements, the ratio of the elongation-to-break value of strands 68 to the elongation-to-break value of strands 62 is at least 5, at least 10, at least 20, less than 100, or less than 50.

Strands 62 may have loops such as loops 64 through which elastic strands 68 pass as strands 68 are intertwined with strands 62 to form fabric 60. The size of loops 64 may be selected to provide fabric 60 with a desired ability to stretch (e.g., so that item 10 may be stretched to fit over a user's hand when placing item 10 on a user's wrist, etc.). During stretching, loops 64 collapse. Conductive strands 66 (e.g., insulated or uninsulated wires with solid cores or polymer cores) may be intertwined with strands 62 on an upper layer of fabric 60 and an opposing lower layer of fabric 60 (e.g., by passing conductive strands 66 through loops 64). There may be more slack in strands 66 than in strands 62, so that when fabric 60 is stretched, strands 62 will be tensioned before strands 66. This will help prevent strands 66 from being overly tensioned and breaking. Conductive strands may be coupled to contacts (terminals) on electrical components in item 10 using solder, welds, conductive adhesive, ball bonding, and/or other conductive joint formation techniques. As shown in FIG. 3, for example, conductive strands 66 may be coupled to contacts 70 on component 72 (e.g., a component in the circuitry of item 10 of FIG. 1).

Antennas 18 may be formed from conductive structures in item 10. As an example, antennas 18 may be formed from metal traces on printed circuit substrates (e.g., flexible printed circuits formed from sheets of polyimide or other flexible polymer or rigid printed circuits formed from fiberglass-filled epoxy or other rigid printed circuit board material). If desired, one or more antennas 18 may be formed from conductive strands in stretchable and/or non-stretchable fabric forming item 10 (see, e.g., conductive paths 50 of FIG. 2). Conductive strands for antennas 18 may be insulated or uninsulated (bare), may have solid metal cores or may be made conductive by coating conductive material such as metal over a polymer core or other dielectric core, and/or may be formed using other conductive strands and/or combinations of strands. Conductive antenna strands may be intertwined with other strands of material for item 10 (see, e.g., fabric 60 of FIG. 3) using weaving, knitting, braiding, sewing, and/or other techniques.

Figure 4:
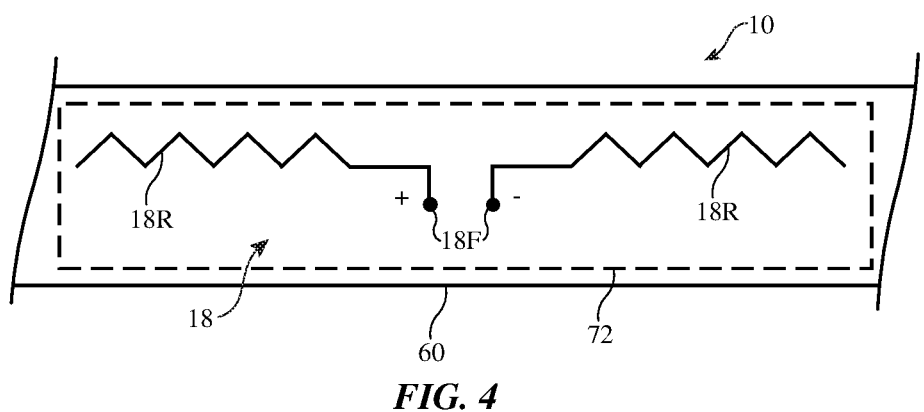
FIG. 4 is a diagram of a portion of a fabric item having an antenna in accordance with an embodiment.

An illustrative portion of item 10 (e.g., fabric for item 10) is shown by fabric 60 of FIG. 4. Fabric 60 may be stretchable fabric (e.g., a stretchable band or other stretchable fabric) or may be non-stretchable fabric. Illustrative antenna 18 of FIG. 4 is a dipole antenna having a pair of antenna resonating element arms 18R. Other types of antenna resonating element (e.g., a slot antenna resonating element, monopole resonating element, inverted-F antenna resonating element, patch antenna resonating element, etc.) may be used in forming antenna 18, if desired. In the example of FIG. 4, resonating element arms 18R have meandering paths (e.g., zig-zag paths) to help enhance the ability of fabric 60 and item 10 to stretch without tensioning the conductive antenna strands. The arms may be about a quarter wavelength in length at the operating frequency of the antenna (e.g., about 80 mm in length in an illustrative configuration in which the antenna is handling radio-frequency signals with a wavelength of about 30 cm and a frequency of about 950 MHz). An optional stiffener such as stiffener (e.g., rigid plastic) may overlap antenna 18 to reduce bending. Antenna 18 may be fed using an antenna feed formed from antenna feed terminals 18F. A transmission line may be used to route antenna signals between feed terminals 18F of antenna 18 and radio-frequency transceiver circuitry 16 (FIG. 1).

Figure 5:
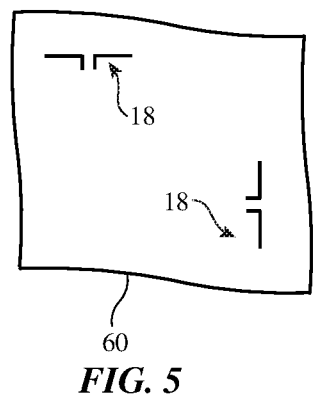
FIG. 5 is a diagram showing how a fabric item may have multiple antennas with different respective orientations in accordance with an embodiment.

If desired, item 10 may be provided with multiple antennas. These antennas may be incorporated into item 10 with diverse locations and/or orientations. During operation, wireless communications circuitry 14 may switch one or more of the antennas into use (e.g., based on signal strength measurements or other suitable antenna selection criteria). FIG. 5 shows how antenna 18 may, as an example, be formed on different portions of fabric 60. Antennas 18 of FIG. 5 are dipole antennas that extend perpendicularly to each other. Other relative orientations may be used for different antennas in item 10, if desired.

Figure 6:
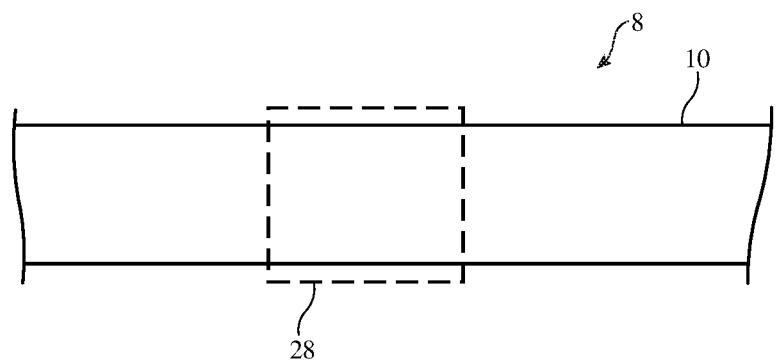
FIG. 6 is a diagram showing how a fabric-based band may be coupled to a housing in accordance with an embodiment.

In some arrangements for system 8, a solid wristwatch unit (e.g., an electronic device with a metal housing or other housing) may be coupled to an elastic band. This type of arrangement is shown in FIG. 6. As shown in FIG. 6, system 8 may include an item with an elastic band such as item 10 (e.g., a wrist band, head band, arm band, waist band, etc.). Electronic device 28 may be a portable electronic device having a solid housing (e.g., a rigid housing formed from metal, plastic, glass, etc.) or other suitable enclosure such as a wristwatch device, cellular telephone, etc. Device 28 may be removably or permanently coupled to item 10 (e.g., device 28 may be incorporated into item 10 by attaching a wristwatch enclosure or other electronic unit to item 10 using fasteners, magnets, lugs, etc.). In this type of arrangement, devices 28 and item 10 may communicate via wired and/or wireless communications. Power may also be shared between device 28 and item 10 via a wired or wireless link.

Figure 7:
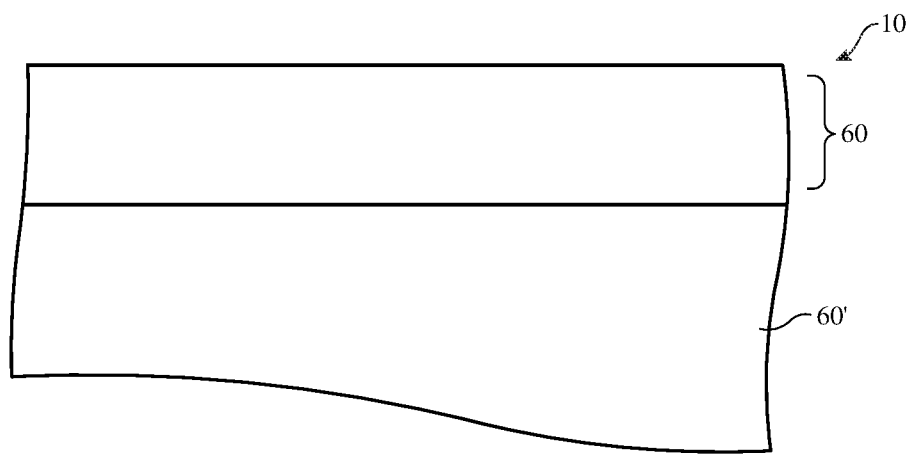
FIG. 7 is a diagram showing how a fabric-based item may have an elastic band coupled to fabric in accordance with an embodiment.

As shown in FIG. 7, item 10 may include a stretchable fabric band (see, e.g., fabric 60) and additional structures such as fabric 60'. Fabric 60' may be stretchable fabric or may not be stretchable. In the arrangement of FIG. 7, fabric 60 may form a stretchable waistband or other stretchable band configured to stretch around a body part of a user and fabric 60' may include fabric for a pair of shorts or other piece of clothing. If desired, fabric 60 may form a stretchable headband and fabric 60' may form a portion of a hat, fabric 60 may form a stretchable arm band and fabric 60' may form part of a shirt, fabric 60 may form a wristband and fabric 60' may form part of a glove, etc.

Figure 8:
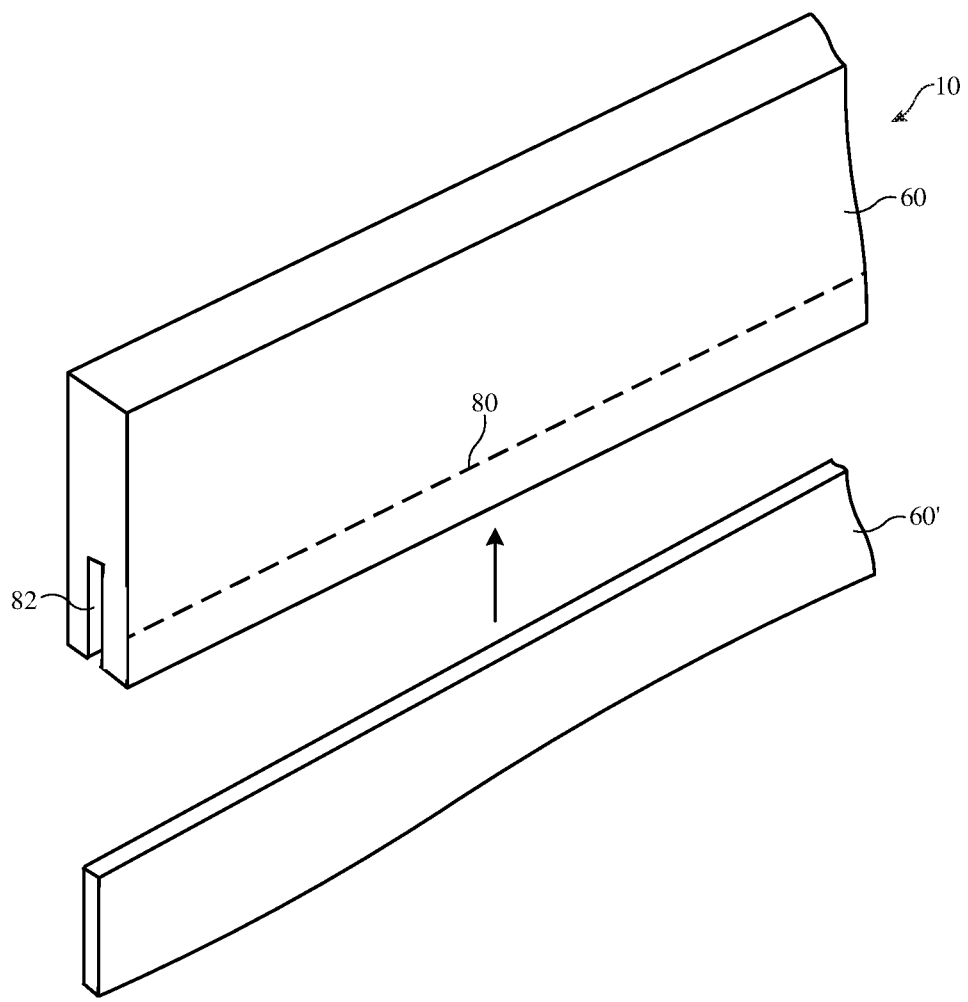
FIG. 8 is an exploded perspective view of an illustrative elastic band and associated fabric showing how the band and fabric may be joined together by sewing in accordance with an embodiment.

If desired, fabric 60 and fabric 60' may be attached by sewing. As shown in FIG. 8, for example, fabric 60' (e.g., fabric that is stretchable or not stretchable) may be inserted in opening 82 of fabric 60 (e.g., a stretchable band) and sewn into place using stitches 80. Fabric 60 and fabric 60' may, if desired, be different types of fabric. As an example, fabric 60 may be a highly elastic band and fabric 60 may be formed from a soft material such as cotton or polymer that is not highly elastic.

The foregoing is merely illustrative and various modifications can be made to the described embodiments. The foregoing embodiments may be implemented individually or in any combination.

What is claimed is:

1. A fabric-based item, comprising:
   a band of stretchable fabric having a ring shape with a central opening configured to surround a body part of a user;
   at least one conductive strand in the stretchable fabric that is configured to form an inductive wireless power receiving coil that runs continuously around the band of stretchable fabric and surrounds the central opening; and
   power receiving circuitry that is coupled to the stretchable fabric and that is configured to receive wireless power using the inductive wireless power receiving coil.

2. The fabric-based item defined in claim 1 wherein the stretchable fabric has first strands with a first elongation-to-break value and second strands with a second elongation-to-break value that is at least five times greater than the first elongation-to-break value and wherein the fabric-based item further comprises electrical components coupled to the stretchable fabric.

3. The fabric-based item defined in claim 2 wherein the first strands comprise nylon, wherein the second strands comprise spandex, and wherein the electrical components comprises electrostatic double-layer supercapacitors.

4. The fabric-based item defined in claim 2 wherein the first elongation-to-break value is less than 50%.

5. The fabric-based item defined in claim 4 wherein the second elongation-to-break value is at least 200%.

6. The fabric-based item defined in claim 2 wherein the electrical components include electrostatic double-layer supercapacitors.

7. The fabric-based item defined in claim 6 wherein the second elongation-to-break value is at least 200%.

8. The fabric-based item defined in claim 2 wherein the electrical components comprise a blood pressure sensor.

9. The fabric-based item defined in claim 2 wherein the electrical components comprise an accelerometer configured to measure a respiration rate.

10. The fabric-based item defined in claim 9, further comprising:
    wireless transceiver circuitry coupled to the stretchable fabric;
    a first antenna coupled to the wireless transceiver circuitry, wherein the first antenna has a first orientation; and
    a second antenna coupled to the wireless transceiver circuitry, wherein the second antenna has a second orientation that is orthogonal to the first orientation.

11. The fabric-based item defined in claim 2 further comprising:
    patch electrodes on the band; and
    conductive paths in the band, wherein the electrical components comprise an electrocardiogram sensor coupled to the patch electrodes by the conductive paths.

12. The fabric-based item defined in claim 1, wherein the power receiving circuitry includes a rectifier that is configured to convert alternating-current power signals received by the inductive wireless power receiving coil into direct-current power.

13. The fabric-based item defined in claim 1, wherein the power receiving circuitry comprises terminals that are configured to receive wired power.

14. An item of clothing configured to be worn on a body part of a user, comprising:
    a ring-shaped stretchable fabric band;
    fabric coupled to the ring-shaped stretchable fabric band;
    wireless transceiver circuitry coupled to the ring-shaped stretchable fabric band;
    a first antenna coupled to the wireless transceiver circuitry, wherein the first antenna has a first orientation and wherein the first antenna has a first antenna resonating element with a meandering path;
    a second antenna coupled to the wireless transceiver circuitry, wherein the second antenna has a second orientation that is orthogonal to the first orientation and wherein the second antenna has a second antenna resonating element with a meandering path;
    control circuitry coupled to the first antenna and the second antenna, wherein the control circuitry is configured to selectively switch the first antenna and second antenna out of use based on signal strength measurements;

an electrostatic double-layer capacitor; and sensor circuitry that is coupled to the ring-shaped stretchable band and that is configured to:

receive power from the electrostatic double-layer capacitor; and gather sensor measurements from the body part.

15. The item of clothing defined in claim 14 further comprising wireless power receiving circuitry having an inductive wireless power receiving coil configured to receive wireless power from a wireless power transmitter.

16. The item of clothing defined in claim 15 wherein the ring-shaped stretchable fabric band includes strands of material having an elongation-to-break value of at least 200% and wherein the sensor circuitry comprises a sensor selected from the group consisting of: a respiration rate sensor, a blood pressure sensor, and an electrocardiogram sensor.

17. The item of clothing defined in claim 14 wherein the first antenna is a dipole antenna and wherein the meandering path of the first antenna resonating element is formed from a conductive strand of material in the ring-shaped stretchable fabric band.

18. A wearable item, comprising:

a stretchable fabric band configured to surround a body part of a user; and circuitry in the stretchable fabric band that comprises:

wireless communications circuitry configured to communicate wirelessly with external electrical equipment;

wireless power receiving circuitry configured to receive wireless power for the circuitry in the stretchable fabric band;

sensor circuitry including an accelerometer configured to measure a respiration rate;

control circuitry configured to use the sensor circuitry to gather measurements from the body part of the user; and haptic output circuitry comprising a vibrator that is configured to vibrate to provide haptic output to the user in response to the measurements from the body part of the user.

19. The wearable item defined in claim 18 wherein the stretchable fabric band comprises intertwined first, second, and third strands, wherein the first strands have an elongation-to-break value of less than 50%, wherein the second strands have an elongation-to-break value of at least 200%, wherein the third strands comprise conductive strands configured to form an inductive wireless power receiving coil, and wherein the wireless power receiving circuitry is configured to receive the wireless power signals using the inductive wireless power receiving coil.

20. The wearable item defined in claim 19 further comprising:

fabric coupled to the stretchable fabric band; and an antenna formed on the fabric, wherein the wireless communications circuitry is configured to communicate with the external electrical equipment using the antenna.

\* \* \* \* \*